United States Patent
Foti

[11] 4,194,512
[45] Mar. 25, 1980

[54] PROBE FOR NYSTAGMUS TESTING

[76] Inventor: Thomas M. Foti, 10937 Deborah Dr., Potomac, Md. 20854

[21] Appl. No.: 804,732

[22] Filed: Jun. 8, 1977

[51] Int. Cl.² ............................................. A61B 5/00
[52] U.S. Cl. ................................... 128/742; 128/746
[58] Field of Search ............ 128/2 Z, 2 R, 2 T, 2 N, 128/1 R, 341–344, 151–152, 303.11–303.12, 399–401; 181/128–135; 179/107 E, 107 R

[56] References Cited

U.S. PATENT DOCUMENTS

| | | | |
|---|---|---|---|
| 789,876 | 5/1905 | Pape | 181/135 |
| 1,040,404 | 10/1912 | Poindexter | 128/341 |
| 1,830,198 | 11/1931 | French | 181/135 |
| 2,633,927 | 4/1953 | Annas et al. | 181/132 |
| 3,581,570 | 6/1971 | Wortz | 73/355 R |
| 3,702,123 | 11/1972 | Macken et al. | 179/107 E |
| 3,848,607 | 11/1974 | St. Clair | 128/400 |
| 3,995,620 | 12/1976 | Epley | 128/2 R |
| 4,029,083 | 6/1977 | Baylor | 128/2 Z |

FOREIGN PATENT DOCUMENTS 2455511  10/1975  Fed. Rep. of Germany ............ 181/135

OTHER PUBLICATIONS

Ono, H. et al, "New Devices for Caloric Test," Fifth Extraordinary Meeting of the Barany Society, Oct. 17–21, 1975.
Kalandadze, A. N., "Method of Closed Calorization of the Ear for Determining the Function of the Vestibular Apparatus".
Foti, T. M. et al., "A Closed Flow Water Caloric System," Jrnl. Nat. Med. Assn., vol. 69, No. 5, May 1977, pp. 303–305.
Ono, H. et al., "A New Caloric Tester Using Ear Canal Balloon," Revue de Laryngologie, Otologie, Rhinologie, May–Jun. 1976, pp. 223–230.

*Primary Examiner*—Robert W. Michell
*Assistant Examiner*—Francis J. Jaworski
*Attorney, Agent, or Firm*—Bacon & Thomas

[57] ABSTRACT

Ear canal caloric testing apparatus includes an ear mold to which a distensible balloon-like receptacle is secured for containing pressurized calorized fluid. Vent passages are provided in the ear mold externally of the receptacle for venting trapped air from the ear canal when the receptacle is distended.

10 Claims, 4 Drawing Figures

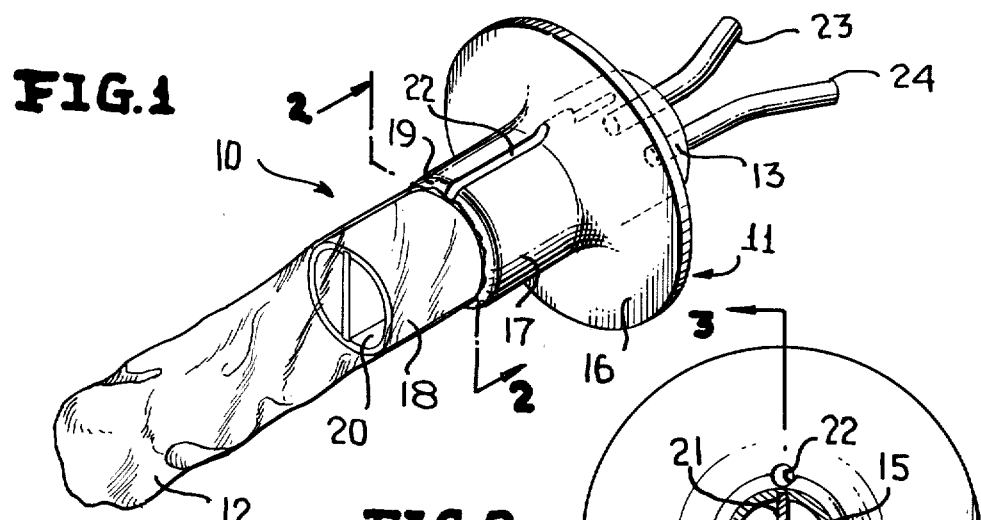
FIG. 1
FIG. 2
FIG. 3
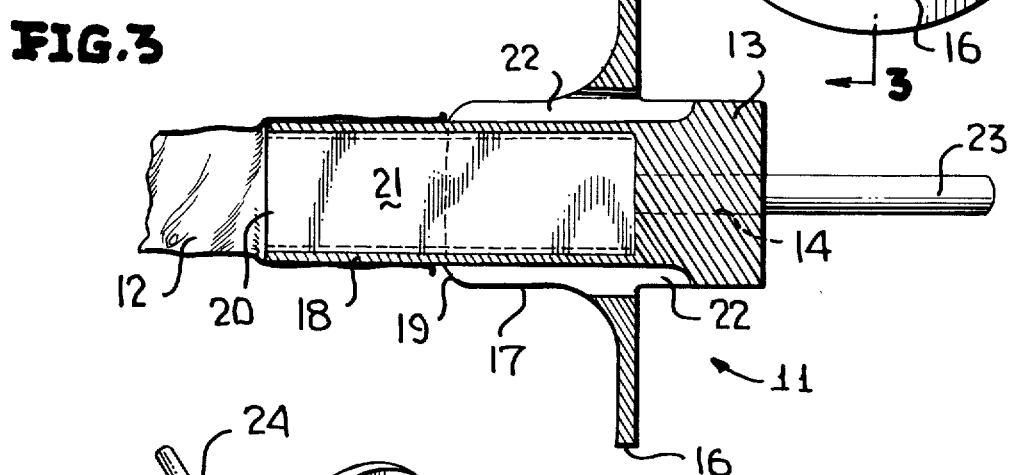
FIG. 4
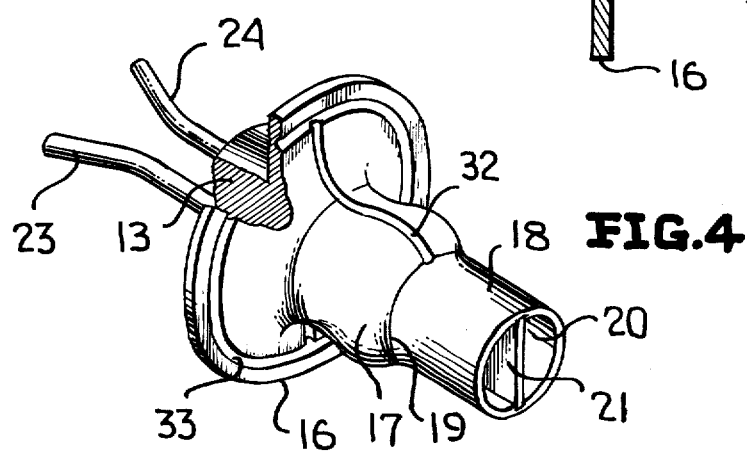

PROBE FOR NYSTAGMUS TESTING

BACKGROUND OF THE INVENTION

The present invention relates to improvements to the Foti probe described in my U.S. patent application Ser. No. 926,718, filed July 21, 1978, entitled "Closed Flow System Method and Apparatus For Inducing Nystagmus," which is a continuation of application Ser. No. 771,340, filed Feb. 23, 1977, now abandoned.

In my aforesaid patent application I describe a membrane-like probe having a flow-through path for nystagmus-inducing liquid, the probe expanding when filled with such liquid to conform to the contours of the ear canal. In one embodiment the insertion depth of the probe is standardized by an ear mold having a widened stop member which limits insertion by abutting the tragus. In order to prevent air from being trapped in the ear canal by the expanding probe, a vent tube extends through the length of the probe to a bore defined through the ear mold.

I have found that the vent tube unnecessarily complicates the construction of the probe and it is an object of the present invention to eliminate the vent tube while still preventing air from being trapped in the ear canal by the expanding membrane.

SUMMARY OF THE INVENTION

In accordance with the present invention, one or more bores or channels are defined in the ear mold to provide venting of the ear canal via the ear mold rather than through the membrane portion of the probe.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein:

FIG. 1 is a view in perspective of the improved probe of the present invention;

FIG. 2 is a view in section taken along lines 2—2 of FIG. 1;

FIG. 3 is a view in section taken along lines 3—3 of FIG. 2; and

FIG. 4 is a partially-cut view in perspective of a modified embodiment of the present invention.

DESCRIPTION OF PREFERRED EMBODIMENTS

For purposes of simplification of the present invention, my aforesaid U.S. patent application Ser. No. 771,340 is incorporated herein by reference.

Referring specifically to FIGS. 1 through 3 of the accompanying drawings, an improved probe is designated generally by the reference numeral 10. Probe 10 includes an ear mold 11 comprising its rearward end and a balloon-like member 12 comprising its forward end. Although preferably formed as an integral member, such as by injection molding techniques or the like, ear mold 11 is described herein as comprising multiple longitudinally-oriented sections. The rearward-most section 13 is, by way of example only, generally cylindrical, with two longitudinally-extending bores 14, 15 defined therethrough. A stop member 16, in the form of an annular flange, extends radially from the forward end of section 13. Immediately forward of stop member 16 is another longitudinally-extending section 17 (cylindrical in the illustrated embodiment) having generally the same diameter as section 13. Extending forwardly of section 17 is the forward-most section 18 of ear mold 11, section 18 also being cylindrical, by way of example only, with a somewhat smaller diameter than section 17. An annular shoulder 19 defines the transition between sections 17 and 18.

A longitudinally-extending bore 20 is defined from the forward end of ear mold section 18 rearwardly through the centers of sections 18 and 17. The forward ends of bores 14 and 15 terminate as openings in the rear wall of bore 20. A flow divider 21 of generally rectangular configuration extends longitudinally through bore 20 to isolate bores 14 and 15 from one another throughout the length of bore 20.

A plurality of longitudinally-extending channels 22 are defined in the surface of ear mold sections 13 and 17. Each channel 22 extends forwardly from section 13, through the base of stop member 16, to section 17 and terminates at annular shoulder 19, thereby providing a flow path from shoulder 19 to rearwardly of the stop member for purposes to be described below.

Flow tubes 23 and 24 are inserted into the rearward ends of bores 14 and 15, respectively. The tubes may be press-fit or adhesively or otherwise secured in the bores. Tubes 23 and 24 serve as inlet and outlet tubes for nystagmus inducing fluid as may be delivered from a suitable pump. An example of such a pump is described in U.S. patent application Ser. No. 762,437, filed Jan. 24, 1977, by George Foti, and entitled "Pump For Closed Circulation System."

Membrane-like balloom member 12 is secured about forward ear mold section 18 and extends forwardly thereof. The open end of the balloon member may be stretch-fitted about section 18 so that member 12 can be disposed of after use and replaced with another balloon member. Alternatively, the balloon member 12 may be permanently secured to section 18, as by adhesive or the like, whereby the probe would be sterilized before re-use. The dimensioning of the balloon member 12 and sections 17 and 18 of the ear mold 11 is such that when member 12 is fully inflated by liquid and the forward end of stop member 16 rests against the tragus of the ear, the inflated member 12 conforms to the external auditory canal and tympanic membrane of the ear.

In operation, nystagmus-inducing liquid flows through inlet tube 23 in bore 14 to one side of bore 20 and is directed by flow divider 21 to membrane 12. Return flow is directed back through the other side of bore 20 to outlet tube 24. Depending upon the temperature of the liquid, thermal transfer from the liquid to the auditory canal is effected through the thin membrane material of member 12 to induce nystagmus in the patient as described in my aforesaid patent application.

The feature of the present invention is the presence of vent passages 22 defined entirely in the ear mold 11. More particularly, when the probe is inserted in a patient's ear, a volume of air is trapped in the ear. This is true if the probe is inserted with member 12 inflated or deflated. Vent passages 22 provide an exhaust path for the trapped air, thereby permitting member 12 to conform fully to the auditory canal and preventing injury to the patient due to pressure build-up. By providing the vent passage in the ear mold only, rather than in the balloon member 12, the configuration of the balloon member is much simpler and the overall probe can be manufactured at less cost.

The vent passages may be defined in the ear mold in other ways than shown in FIGS. 1-3. The important point is that the vent passage is defined only in the ear mold and not through member 12. An example of another approach to forming the vent passages is shown in FIG. 4. Specifically probe 30 has elements which are identical to those in probe 10 and are designated by the same reference numerals. The difference resides in the fact that the longitudinal vent passages are not defined in rearward section 13. Instead, vent passages 32 are defined longitudinally along section 17 and extend radially along the forward surface of stop member 16, terminating in an annular channel 33 which is disposed concentrically near the outer edge of the stop member. Stop member 16 in probe 30 is provided with a slight rearward taper so that only the base of that member abuts the patient's tragus while the radially outer portion is separated from the tragus. Air trapped by the probe in the patient's ear can therefore escape by travelling along passages 32 to annular channel 33 which communicates with ambient.

While I have described and illustrated one specific embodiment of my invention, it will be clear that variations of the details of construction which are specifically illustrated and described may be resorted to without departing from the true spirit and scope of the invention as defined in the appended claims.

I claim:

1. Apparatus for transferring thermal energy from a test fluid to an ear canal of a patient comprising:
   a expansible receptacle for said test fluid, said receptacle being sufficiently small to be inserted into said ear canal and sufficiently flexible to be expanded to conform to at least a portion of said ear canal upon internal pressurization of said receptacle by said test fluid;
   wherein said receptacle is made from plastic of membrane-like thickness to permit efficient transfer of thermal enery therethrough from test fluid in said receptacle;
   an inlet passage for delivering test fluid under pressure into said receptacle;
   an outlet passage for conducting test fluid under pressure out of said receptacle;
   an ear mold secured to said receptacle, said ear mold having a forward section insertable into said ear canal, said mold adapted to be partially inserted into said ear canal with said forward section and said receptacle extending further into said ear canal, said receptacle attached to said forward section in sealing relationship and
   vent passage means defined in the forward section of said ear mold externally of said receptacle for exhausting air from around the exterior of said receptacle in the area of said forward section to ambient.

2. The apparatus according to claim 1 wherein said vent passage means comprises at least one channel defined in the surface of said ear mold extending between said forward section and ambient.

3. The apparatus according to claim 1 wherein said ear mold includes a widened stop portion to preclude insertion of said ear mold and receptacle beyond a predetermined depth into said ear canal, and wherein said vent passage means comprises a plurality of channels defined in the ear mold surface forward of said stop portion and communicating with holes defined through said stop portion, said channels extending between said forward section and said holes.

4. The apparatus according to claim 1, wherein said ear mold includes a widened stop portion to preclude insertion of said ear mold and receptacle beyond a predetermined depth into said ear canal, and wherein said vent passage means includes channels defined in the surface of said stop portion of said ear mold forward of said stop portion, said channels extending between said stop portion and said forward section.

5. The apparatus according to claim 1 wherein said vent passage means comprises plural longitudinally-extending channels defined in the surface of said ear mold, said channels extending between said forward section and ambient.

6. The apparatus according to claim 5 wherein said ear mold includes a widened stop portion to preclude insertion of said ear mold and receptacle beyond a predetermined depth into said ear canal, and wherein said channels extend through holes defined in said stop portion.

7. The apparatus according to claim 1 wherein said receptacle is removably secured to said ear mold to permit replacement of said receptacle after use.

8. Apparatus for performing caloric nystagmus testing on a patient comprising:
   an ear mold including a forward section insertable into a patient's ear canal;
   a expansible balloon-like receptacle attached to said forward section in sealed relationship and adapted to be inserted into said canal with said forward section;
   means for conducting calorized test fluid into said receptacle through said ear mold without contact between test fluid and the patient's ear canal for transferring thermal energy between the test fluid in said receptacle and the patient's ear canal; and
   venting means defined in the forward section of said ear mold externally of said receptacle for conducting air from around the exterior of said receptacle in said ear canal to ambient, said venting means providing communication between said forward section and ambient.

9. The apparatus according to claim 8, said receptacle being secured about and enclosing at least part of said forward section, while extendable freely forwardly of the ear mold.

10. The apparatus according to claim 9, said venting means comprising a depressed channel extending along the length of the ear mold from the juncture of said forward section and the ear mold structure next rearwardly thereof, said channel being in communication with ambient.

* * * * *